excluded page type: cover page / title page

METHOD OF PREPARING ESTERS OF ARYLOXYPHENOXY PROPANOIC ACID

CROSS-REFERENCE TO RELATED APPLICATION

This application is a continuation-in-part of Ser. No. 494,196 filed May 13, 1983, now abandoned.

BACKGROUND OF THE INVENTION

The present invention is directed to an improved method of preparing esters of aryloxyphenoxy propanoic acids. In particular, the present invention is directed to an improved method of preparing esters of pyridyloxyphenoxy propanoic acids. The aryloxyphenoxy propanoic acid esters produced by the present invention are useful are herbicides.

Aryloxyphenoxy propanoic acid esters are generally prepared by a three step process involving the neutralization of hydroquinone followed by coupling with an aryl halide and then reacting the resulting aryloxyphenate with an appropriate halopropionate in an inert solvent at an elevated temperature in the presence of an alkaline material. An excess molar quantity of the halopropionate is usually employed because of competing side reactions. Because an excess of halopropionate is desired, an almost instantaneous addition of halopropionate to the aryloxyphenate is required. This is impractical upon scale-up to commercial production so the aryloxyphenate must be added to the halopropionate. Since the aryloxyphenate must invariably be prepared from the reaction of an aryl halide with hydroquinone due to the lack of commercial availability of aryloxyphenates in large quantities, a second reaction vessel is required so that the aryloxyphenate may be added to the halopropionate.

U.S. Pat. No. 4,046,553 teaches a method of preparing α-[4-(5-mono-substituted or 3,5-di-substituted-pyridyl-2-oxy)phenoxy]alkanecarboxylic acid esters by reacting a pyridyloxyphenol with a haloalkanecarboxylate in the presence of an alkaline material at a temperature of about 40° C.–120° C. See Column 11, lines 24–47; Column 12, lines 35–57; and Preparation Examples 1 and 4.

British Patent Specification 1,599,121 teaches a method of preparing α-[4-(5-trifluoromethyl-2-pyridyloxy)phenoxy]alkane carboxylic acid esters by reacting a substituted pyridyloxyphenol with a haloalkanecarboxylate in the presence of an alkaline material at a temperature of 40° C.–200° C. See Page 7, line 30 to Page 8, line 6; Page 8, lines 25 to 36; and Preparation Examples 1 and 3.

U.S. Pat. Nos. 4,214,086 and 4,275,212 teach methods of preparing aryloxyphenols by reacting aryl halides with hydroquinone in the presence of a base such as NaOH or KOH. These reactions result in the formation of water.

U.S. Pat. No. 4,325,729 teaches a method of preparing pyridyloxyphenoxy propionates by reacting a pyridyloxyphenol with an α-halogencarboxylic acid derivative in the presence of a base. Reaction temperatures are indicated between 0° C.–200° C.

The present methods known to prepare aryloxyphenoxy propanoic acid esters by reacting an aryloxyphenate with a halopropionate, including those described above, suffer from disadvantages, such as, side reactions resulting in the formation of undesirable by-products and a rather low conversion (75–80%) of the starting materials to the desired products. A base, such as, sodium or potassium carbonate, is usually added to the reactants to increase the conversion to 99+% but introduces a solid waste problem. Because of the occurrence of side reactions, an excess of halopropionate is normally employed which introduces purification steps and additional process steps for the recovery of the excess halopropionate.

The present invention remedies the above problems encountered in the preparation of esters of aryloxyphenoxy propionic acid. It has been discovered that water is a major cause of side reactions and is responsible for the low conversion of the starting materials. It has also been discovered that elevated temperatures enhance the formation of a bis(aryloxy)benzene by-product. The formation of this bis by-product is reduced when the third step of the reaction sequence is carried out at a temperature below about 35° C. The combination of a low water level reaction and a low temperature reaction results in advantages, such as: the elimination of the need for additional base; a higher yield based on the propionate starting material; a one vessel reaction; the elimination of the step to recover excess propionate since near stoichiometric amounts of the propionate are employed; and a reduction in the side reactions (by-products) caused by high temperature and high water levels.

SUMMARY OF THE INVENTION

The present invention provides a one-pot method of preparing aryloxyphenoxy propionic acid esters. The improvements are (a) conducting the third step of the reaction sequence in the presence of less than about 1,000 parts per million by weight (ppm) water and (b) also conducting the third step of the reaction at a temperature below about 35° C. Each improvement, separately, is responsible for less by-product formation thereby resulting in an improved yield of the desired aryloxyphenoxy propionic acid ester. The improvements may be practiced separately but are preferably combined and practiced together in a single operation.

Of particular interest in the practice of the present invention is an improved method of preparing an ester of 2-(4-(((3-chloro-5-trifluoromethyl)-2-pyridinyl)oxy)-phenoxy)propanoic acid, commonly known as haloxyfop; 2-(4-(((3-fluoro-5-trifluoromethyl)-2-pyridinyl)oxy)phenoxy)propanoic acid; or 2-(4-(((5-trifluoromethyl)-2-pyridinyl)oxy)phenoxy)propionic acid, commonly known as fluazifop. Esters of particular interest include the methyl, n-butyl, methoxypropyl and ethoxyethyl esters.

DETAILED DESCRIPTION OF THE INVENTION

More particularly, the present invention provides a method of preparing an ester of an aryloxyphenoxy propanoic acid of the formula

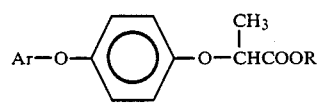

wherein
Ar represents an aryl group; and
R represents $C_1$–$C_8$ alkyl or $C_3$–$C_6$ alkoxyalkyl;
which comprises forming

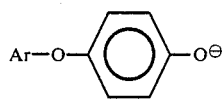

wherein
Ar is as defined above;
by the reaction of ArX with the dianion of hydroquinone, reducing the water content of the reaction mixture to less than 1,000 ppm and thereafter, without isolation of the phenate intermediate, reacting with an excess stoichiometric amount of a propionate of the formula

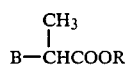

wherein
R is as defined above; and
B represents Cl or Br.

An additional improvement in the present reaction is achieved when the reaction is conducted at a temperature below about 35° C. Preferably, both the low water (<1,000 ppm) and low temperature (<35° C.) reaction conditions are carried out together in the same reaction resulting in an improved yield of the desired product.

LOW-WATER CONDITION

The low-water reaction condition can be achieved by distilling off water present in the aryloxyphenate/inert medium mixture before the propionate reactant is added. The water is distilled off until the water level in the reaction mixture is less than about 1,000 ppm, advantageously less than about 500 ppm, preferably less than about 250 ppm and most preferably less than about 125 ppm.

Water can be introduced into the reaction mixture in a number of ways. The most common way water is introduced into the reaction mixture is from the preparation of the aryloxy phenate. The reaction of hydroquinone with a base, such as, NaOH, KOH or NH$_4$OH, in an inert carrier, forms a hydroquinone dianion and water. This hydroquinone dianion is reacted with an arylhalide to form the aryloxyphenate starting material. Attempts to distill the water out of the hydroquinone dianion/carrier reaction mixture after formation of the hydroquinone dianion but before the reaction with the arylhalide fail to get the water level below about 2,000 ppm. It has been surprisingly found that the addition of an effective amount of methanol to the hydroquinone dianion/carrier/water reaction mixture will promote the distillation of the water from the reaction mixture. The methanol will distill first, followed by the water, second. Usually methanol is added to the reaction mixture in an amount by weight that is at least about equivalent to the amount of water by weight that will be in the reaction mixture after formation of the hydroquinone dianion. Preferably, the weight ratio of methanol:water in the reaction mixture will be about 2:1.

It has also been surprisingly found that distillation after the hydroquinone dianion is reacted with the aryl halide to form the aryloxyphenate removes water from the reaction mixture to levels about 1,000 ppm or less. If the distillation is carried out long enough, water levels of about 125 ppm or less are achievable.

Alternatively, low water levels are achieved by preparing the hydroquinone dianion by reacting hydroquinone with an alkali metal alkoxide, such as, for example NaOCH$_3$, KOCH$_3$, NaOCH$_2$(CH$_2$)$_2$CH$_3$, KOCH$_2$(CH$_2$)$_2$CH$_3$, KOC$_2$H$_5$ or NaOC$_2$H$_5$, in an inert medium such as, for example dimethylsulfoxide (DMSO), whereby the hydroquinone dianion and the corresponding alcohol are formed. This procedure avoids the formation of water in the preparation of the hydroquinone dianion. The resulting alcohol is readily distilled off from the reaction mixture.

The metal alkoxides employed in preparing the hydroquinone dianion are well known compounds and can be prepared employing well known techniques. Suitable metal alkoxides include, for example, alkali metal alkoxides, such as, NaOCH$_3$, NaOCH$_2$(CH$_2$)$_2$CH$_3$ and NaOC$_2$H$_5$. NaOCH$_3$ and HaOC$_2$H$_5$ are prepared by reacting sodium metal with anhydrous methanol, n-butanol or ethanol to make a solution of the corresponding alkoxide in the corresponding alcohol. The metal alkoxide solution is reacted with hydroquinone under N$_2$ in an inert medium (DMSO) to make the hydroquinone dianion. The alcohol is then distilled off and the hydroquinone dianion is reacted with an aryl halide to form the aryloxyphenate starting material whereby substantially no water is present in the reaction mixture.

LOW-TEMPERATURE CONDITION

Because the present reaction is exothermic, the low temperature reaction condition can be achieved by (1) adding the propionate starting material slowly to the aryloxyphenate so that the temperature of the reaction mixture does not exceed about 35° C. or (2) cooling the reaction mixture with an external cooling means so that the reaction mixtures does not exceed about 35° C. Advantageously, the reaction mixture is maintained throughout the reaction at a temperature below about 30° C. and preferably at or below about 25° C.

Suitable for use as an inert carrier medium are polar aprotic solvents, such as, DMSO, dimethylformamide (DMF), dimethylacetamide, diethylacetamide, sulpholane and N-methylpyrrolidinone. A preferred inert carrier medium is DMSO.

The present improvements provide a reaction wherein less by-product formation is observed but provides about a 95% conversion of the aryloxyphenate starting material. To drive the reaction to completion an effective amount of a hindered non-nucleophilic phenol, which is converted in situ to the phenate form, is added to the reaction. An effective amount of a hindered phenol will drive the reaction to 99+% conversion. A preferred hindered phenol is 2,6-di-t-butyl-4-methyl phenol (BHT). Usually at least about 0.05 mol of hindered non-nucleophilic phenol per mole of aryloxyphenate is added to the present reaction, i.e., about 5 mol percent.

When a metal or ammonium hydroxide or an alkoxide is reacted with hydroquinone to form the hydroquinone dianion, a slight excess hydroxide or alkoxide is advantageously employed. This slight excess of hydroxide or alkoxide converts the hindered non-nucleophilic phenol in situ to the phenate form. A hindered non-nucleophilic phenol can be added to the hydroxide or alkoxide and hydroquinone reactants in an amount that is about equivalent to the slight excess of hydroxide or alkoxide. For example, if 2.05 mols of NaOH are reacted with 1.0 mol of hydroquinone, then about 0.05 mol of hindered non-nucleophilic phenol is added to the reactants which is thereafter reacted with the aryl halide to form the aryloxyphenate. Upon addition of the propionate, and without isolation of the phenates, a 99+% conversion of starting materials is achieved.

Suitable aryloxyphenate reactants for the second step of the reaction sequence include quinolinyloxyphenates, phenyloxyphenates, pyridyloxyphenates, quinoxalinyloxyphenates, benzoxazoloxy phenates and benzothiazolyloxyphenates. Preferred reactants for the second step of the reaction sequence include 4-(pyridyl-2-oxy)phenates of the formula

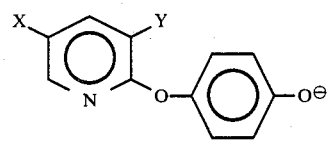

wherein X and Y each independently represents $CF_3$, H, Cl, F, Br or I. The aryloxyphenates described above are known compounds and can be prepared employing techniques well-known in the art, such as, for example by the reaction of an arylhalide with the dianion of hydroquinone.

Suitable propionate reactants include compounds of the formula

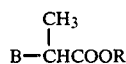

wherein
  B represents Cl or Br; and
  R represents $C_1$–$C_8$ alkyl or $C_3$–$C_6$ alkoxyalkyl.

These propionate reactants are for the most part known compounds and can be prepared employing techniques well-known in the art. Preferred propionates are those compounds wherein R is n-butyl, methyl, methoxypropyl ($C_3H_6OCH_3$) or ethoxyethyl ($C_2H_4OC_2H_5$). Methoxypropyl propionates are compounds of the formula

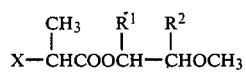

wherein
  X represents —Cl or —Br;
  $R^1$ represents —H or —$CH_3$; and
  $R^2$ represents —H or —$CH_3$;
with a first proviso that when $R^1$ is —H, then $R^2$ is —$CH_3$ and a second proviso that when $R^1$ is —$CH_3$ then $R^2$ is —H.

Such compounds are prepared by employing procedures analogous to standard, well-known procedures used for preparing structurally related compounds. For example, such compounds can be prepared by the acid catalyzed esterification of a 2-substituted propionic acid.

Such compounds can also be prepared by the transesterification of the methyl ester of a 2-substituted propionic acid employing an alkyl titanate catalyst.

The reaction of the present invention can be characterized by the following chemical equation:

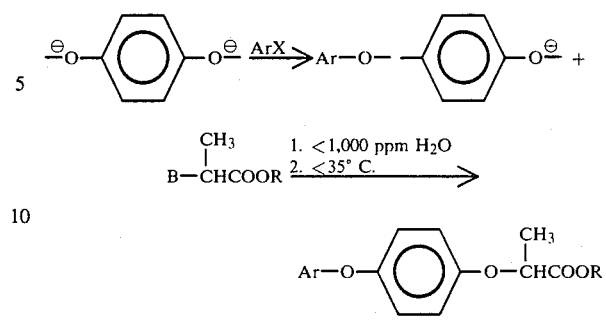

wherein Ar represents phenyl, pyridyl, quinolinyl, quinoxalinyl, benzoxazolyl or benzothiazolyl and B and R are as defined above. No attempt has been made to balance the above equation. A hindered non-nucleophilic phenol, which is converted into the phenate form in situ, may be added to the reactants to drive the reaction to 99+% conversion.

In one embodiment of the present invention, 4-(5-(trifluoromethyl)pyridinyl-2-oxy)phenate is prepared and reacted in situ with an appropriate propionate, employing the low water and low temperature conditions described herein, resulting in the formation of the corresponding ester of 2-(4-(((5-trifluoromethyl)-2-pyridinyl)oxy)phenoxy)propionic acid. The third step of this reaction sequence can be characterized as follows:

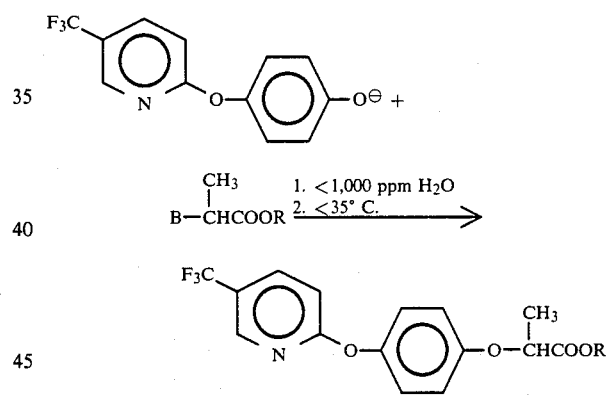

wherein B and R are as hereinbefore defined.

In a preferred embodiment of the present invention, 4-(3-chloro-5-(trifluoromethyl)pyridinyl-2-oxy)phenate is prepared and reacted in situ with an appropriate propionate, employing the low-water and low temperature conditions described herein, resulting in the formation of the corresponding ester of 2-(4-(((3-chloro-5-trifluoromethyl)-2-pyridinyl)oxy)phenoxy)propionic acid. The third step of this reaction sequence can be characterized as follows:

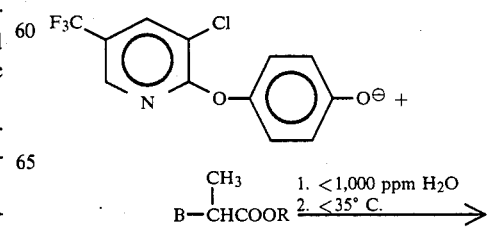

-continued

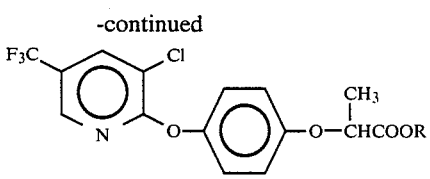

wherein B and R are as hereinbefore defined.

In another embodiment of the present invention, 4-(3-fluoro-5-(trifluoromethyl)pyridinyl-2-oxy)phenate is prepared and reacted in situ with an appropriate propionate, employing the low-water and low temperature conditions described herein, resulting in the formation of the corresponding ester of 2-(4-(((3-fluoro-5-trifluoromethyl)-2-pyridinyl)oxy)phenoxy)propionic acid.

Once prepared, the aryloxyphenoxy propionates formed by the present reaction are recovered employing standard, well-known, extraction and purification techniques, such as, for example, solvent extraction with methylene chloride.

The following examples illustrate the practice of the present invention but should not be construed as limiting its scope. No attempt has been made to balance any chemical equations described herein. Water level determinations were made by the KARL-FISHER method.

EXAMPLE 1

A 250 milliliter (ml), 3-neck, round bottom flask, equipped with a thermowell, addition funnel, air-driven stirrer and a 20 centimeter (cm)×1 cm vigreaux column with distillation head, was purged with $N_2$ and loaded with 100 ml of DMSO and 11 grams (g) (0.1 mol) of hydroquinone. The addition funnel was loaded with 16 g of 50% NaOH (0.2 mol). The flask was heated to approximately 60° C. where the system was degassed by pulling a vacuum until the DMSO started boiling and then releasing the vacuum with $N_2$. The system was degassed three (3) times in this manner and the vacuum was set at approximately 100 millimeters (mm). The temperature was increased to approximately 95° C. and the NaOH was added over a 5-10 minute period causing the dianion of hydroquinone to precipitate. The temperature was increased to distill off the water at a pot temperature of approximately 105°-125° C. and a head temperature of 50°-124° C. When only DMSO was coming overhead (about 25 g of distillate), the temperature was decreased to approximately 80° C. and the vacuum was released to $N_2$. Keeping the temperature of the reaction mixture below 90° C., 21.6 g (0.1 mol) of 2,3-dichloro-5-(trifluoromethyl)pyridine was added over a 10-20 minute period. The reaction mixture was kept at a temperature between 80°-90° C. for 1-1½ hours whereby 4-(3-chloro-5-(trifluoromethyl)pyridyl-2-oxy)phenate was formed. At this point the reaction mixture contained from 2,000-5,000 ppm water. About 30-50 g of DMSO was distilled off from the reaction mixture at 80° C./15 mm which reduced the water level from 5,000 ppm to less than about 120 ppm. The reaction mixture was cooled to 25° C. and 13.5 g (0.11 mol) of methyl 2-chloropropionate was added over a 15 minute period so that the temperature remained under 30° C. After 5 hours at room temperature, the conversion of 4-(3-chloro-5-(trifluoromethyl)pyridyl-2-oxy)pheneate to 2-(4-((3-chloro-5-trifluoromethyl)-2-pyridinyl)oxy)phenoxy)propionic acid, methyl ester was 96%. The product mixture was filtered. The precipitate was washed with four (4) 25 ml portions of methylene chloride. The combined filtrates were extracted with one (1) 50 ml and three (3) 20 ml portions of water. The water was made acidic with HCl to break emulsions. The organic phase was solvent stripped on a rotavap at 70° C./20 mm for 30 minutes to give 37 g of crude product assaying at approximately 91% 2-(4-((3-chloro-5-trifluoromethyl)-2-pyridinyl)oxy)phenoxy propionic acid, methyl ester. The unoptimized yield based on propionate was 81.5 percent.

EXAMPLE 2

Sodium metal was added to methanol to make a 20% by weight solution of $NaOCH_3$ in methanol. 54 g (0.2 mol $NaOCH_3$) of the $NaOCH_3$ in methanol solution was placed in an $N_2$ purged flask with 0.1 mol hydroquinone and 100 ml DMSO. Most of the alcohol was stripped out at atmospheric pressure until the pot temperature reached approximately 130° C. The pot was cooled to approximately 60° C. and put under a 100 mm vacuum. The remaining alcohol was taken overhead until only DMSO was coming overhead. 21.6 g (0.1 mol) of 2,3-dichloro-5-(trifluoromethyl)pyridine was added to the reaction mixture resulting in the formation of 4-(3-chloro-5-(trifluoromethyl)pyridyl-2-oxy)phenate. At this point the water content of the reaction mixture was 100-250 ppm $H_2O$. Substantially the same procedures described in Example 1 were repeated resulting in the formation of 2-(4-((3-chloro-5-trifluoromethyl)-2-pyridinyl)oxy)phenoxy propionic acid, methyl ester in a good yield.

EXAMPLE 3

A mixture of DMSO (1089 g), hydroquinone (88.0 g; 0.80 mol) and IONOL® brand 2,6-di-tert-butyl-4-methylphenol (8.8 g; 0.04 mol) was distilled at ~35 mm for 1.5 hours (Pot=105° C.; Head=99° C.). 249 g of distillate was collected. The temperature of the mixture was reduced to 85° C. and 336.5 g (1.63 mols) of sodium methoxide in methanol (26.2% by weight) was added to the mixture rapidly. The mixture was then heated under $N_2$ for one (1) hour resulting in 229.4 g of methanol distillate (Pot=103°-138° C.; Head=66° C.). The mixture was cooled to 85° C. Under a vacuum of 100 millimeters (mm) the mixture was further distilled for an additional hour resulting in 136.3 g of methanol distillate (Pot= 125° C.; Head=124° C.). The temperature of the mixture was lowered to 80° C. and 2,3-dichloro-5-(trifluoromethyl)pyridine (169.0 g; 0.7566 mol) of 97% purity was added to the mixture over a 20 minute period. The mixture was continuously mixed for two (2) hours resulting in the formation of 4-(3-chloro-5-(trifluoromethyl)pyridyl-2-oxy)phenate. At this point the water level in the reaction mixture was determined to be 381 ppm. The temperature of the reaction mixture was reduced to 25° C. and methyl 2-chloropropionate (100.7 g; 0.822 mol) was added to the reaction mixture over a 35 minute period whereby the temperature of the reaction mixture fluctuated between 20° C. and 28° C. After 45 minutes of continuous stirring, analysis of the reaction mixture indicated a 99+% conversion of the 4-(3-chloro-5-(trifluoromethyl)pyridyl-2-oxy)phenate. The reaction mixture (1116 g) was continuously stirred overnight. In the morning, the reaction mixture was diluted and mixed with 700 ml of perchloroethylene, 350 ml of $H_2O$ and 15 ml of concentrated HCl resulting in the formation of 3 layers: a top organic layer, a middle emulsion layer and a bottom aqueous layer. The organic layer was separated and the aqueous and emulsion layers were diluted and mixed with 200 ml of perchloroethylene, 100 ml of H$_2$O and 5 ml of concentrated HCl resulting in the formation of 3 layers again. The organic layers were combined and extracted with two (2) 500 ml portions of H$_2$O. The solvent was stripped at 90° C./20 mm for 1.5 hours to give 343.3 g of product containing 77.2% by weight of 2-(4-(((3-chloro-5-trifluoromethyl)-2-pyridinyl)oxy)phenoxy propionic acid, methyl ester. This represents a yield of 92.9% of theoretical based on the 2,3-dichloro-5-(trifluoromethyl)-pyridine starting material and an optimized yield of 85.9% of theoretical based on the methyl 2-chloropropionate starting material.

EXAMPLE 4

Substantially the same procedures described in Example 3 were repeated except that ethoxy ethyl 2-chloropropionate was employed instead of methyl 2-chloropropionate. The resulting product, i.e., 2-(4-((3-chloro-5-trifluoromethyl)-2-pyridinyl)oxy)phenoxy propionic acid, ethoxy ethyl ester, was formed in a good yield (92% based on pyridine starting material). The unoptimized yield based on propionate was 81 percent.

EXAMPLE 5

A mixture of DMSO (360 ml), hydroquinone (55.0 g; 0.5 mol), IONOL ® brand BHT (5.7 g; 0.026 mol) and anhydrous methanol (135 ml) was degassed at room temperature and left under an N$_2$ atmosphere. Aqueous NaOH (82.7 g; 1.025 mols) (49.5% by weight) was added to the mixture and the mixture was distilled for one (1) hour and 10 minutes (Pot=110° C.-130° C.; Head=64°-72° C.). 95 ml of distillate was collected which contained 9% by weight water. A total of 120 ml of DMSO was continuously fed into the mixture during the distillation. The temperature of the reaction mixture was decreased to <80° C. Under a vacuum of 95 mm the mixture was further distilled for 4 hours (Pot=80° C.-125° C.; Head=32°-123° C.) resulting in 310 g of distillate. The mixture was cooled and 2,3-dichloro-5-(trifluoromethyl)pyridine (102.5 g; 0.46075 mol) of 97% purity was added to the reaction mixture. The mixture was kept at 95° C., with continuous stirring for 4 hours and 10 minutes. At this point, the reaction mixture contained 497 ppm water. The mixture was cooled to about 25° C. and methyl 2-chloropropionate (66.1 g; 0.54 mol) was added over a 5 minute period whereby the temperature of the mixture was kept under 27° C. The mixture was stirred at room temperature overnight. The desired product was then recovered by solvent extraction, employing methylene chloride and acidified water, in a yield of 90.5% of theoretical based on the 2,3-dichloro-5-(trifluoromethyl)pyridine starting material. The unoptimized yield based on propionate was 77 percent.

EXAMPLE 6

Sodium hydroxide pellets (10.94 g; 0.26 mol) containing about 95% NaOH and 65 ml of anhydrous methanol were mixed and stirred overnight under N$_2$. In the morning, hydroquinone (14.0 g; 0.127 mol), IONOL ® brand BHT (1.50 g; 0.0068 mol) and 130 ml of DMSO were mixed and added rapidly to the NaOH/methanol mixture. The reaction mixture was kept under N$_2$, heated and distilled for 2.25 hours (Pot=130° C.; Head=60°-64° C.). The mixture was cooled to <80° C. and put under a vacuum of 105 mm. The mixture was reheated. Distillation occurred for 1.5 hours, stopped for about 2 hours, then occurred again for 45 minutes (Pot=80°-123° C.; Head=55°-112° C.). The distillate in the last 45 minutes weighed about 30 g and was mostly DMSO. 2,3-Dichloro-5-trifluoromethyl)pyridine (26.7 g; 0.12028 mol) of 97% purity was added to the reaction mixture over a 5 minute period. The reaction mixture was stirred continuously at 85°-90° C. for one (1) hour and 35 minutes. Analysis of the reaction mixture indicated there was about 495 ppm H$_2$O. The reaction mixture was cooled to 25° C. and methyl 2-chloropropionate (17.2 g; 0.14 mol) was added. The reaction mixture was left at room temperature overnight with continuous stirring. Analysis indicated a 99+% conversion of 4-(3-chloro-5-(trifluoromethyl)-pyridyl-2-oxy)phenate. The unoptimized yield based on propionate was 71.4 percent.

EXAMPLE 7

IONOL ® brand BHT (1.11 g; 0.005 mol) and hydroquinone (11.0 g; 0.10 mol) were dissolved in 100 ml of DMSO in a N$_2$ purged flask. Sodium methoxide (42.25 g of a 26.2% CH$_3$O$^\ominus$/CH$_3$OH solution; 0.205 mol) was added to the reaction mixture. The reaction mixture was distilled for 1 hour and 10 minutes under a 100 mm vacuum (Pot=55°-124° C.; head=23°-124° C.). The reaction mixture was cooled to 58° C. and 2-chloro-5-(trifluoromethyl)pyridine (18.2 g; 0.10 mol), dissolved in 10 ml of DMSO, was added thereto. The reaction mixture was heated to between 80°-90° C. for 2 hours. At this point, the reaction mixture contained 120 ppm H$_2$O. The reaction mixture was cooled to 20° C. and n-butyl 2-chloro-propionate (18.1 g containing 220 ppm H$_2$O; 0.11 mol) was added to the reaction mixture while the temperature of the reaction mixture was maintained at room temperature with continuous stirring for 2.5 hours. Analysis indicated a 99+% conversion and a yield of about 95% based on pyridine. The yield based on propionate was 86 percent.

Various other aryloxyphenoxy propionic acid esters, described herein, are made in a good yield when low water levels and low temperatures, as described herein, are employed in the reaction of the appropriate aryloxyphenol with the appropriate propionate.

I claim:
1. In a method of preparing an ester of an aryloxyphenoxy propanoic acid of the formula

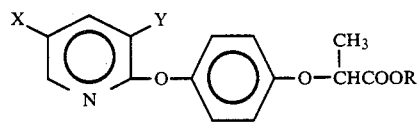

wherein
X represents H, CF$_3$, Cl, F, Br or I;
Y represents Cl, H, F, Br, CF$_3$ or I and
R represents C$_1$-C$_8$ alkyl or C$_3$-C$_6$ alkoxyalkyl;
which comprises forming

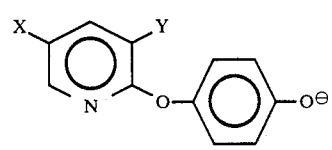

by the reaction of

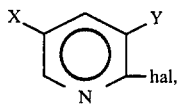

wherein X and Y are as defined above and hal is Cl, F, Br, or I,
with the dianion of hydroquinone under an inert atmosphere while maintaining the water content of the reaction mixture at less than 1,000 ppm and thereafter, without isolation of the phenate intermediate, reacting with an excess stoichiometric amount of a propionate of the formula

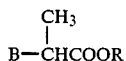

wherein
R is as defined above; and
B represents Cl or Br
at a temperature that does not exceed 35° C.

2. Method of claim 1 wherein the dianion of hydroquinone is formed by the reaction of hydroquinone with an alkali metal alkoxide.

3. Method of claim 2 wherein the alkali metal alkoxide is sodium methoxide.

4. Method of claim 1 wherein the dianion of hydroquinone is formed in an inert carrier/water reaction mixture and methanol is added to facilitate the removal of water by distillation.

5. The method of claim 1 wherein X is $CF_3$ and B is Cl or Br.

6. The method of claim 5 wherein Y is H or Cl.

7. The method of claim 6 wherein R is $CH_3$, n-butyl, $C_3H_6OCH_3$ or $C_2H_4OC_2H_5$.

8. The method of claim 7 wherein the water content is about 500 ppm or less.

9. The method of claim 8 wherein the water content is about 250 ppm or less.

10. The method of claim 9 wherein the water content is about 125 ppm or less.

11. The method of claim 8 wherein Y is Cl.

12. The method of claim 11 wherein R is $CH_3$ or $C_2H_4OC_2H_5$.

13. The method of claim 8 wherein Y is H.

14. The method of claim 13 wherein R is n-butyl.

15. The method of claim 1 comprising a third improvement of adding to the reactants an amount of a hindered non-nucleophilic phenol, which converts in situ to the phenate form, effective to drive the reaction to greater than 99 percent conversion.

16. The method of claim 15 wherein the hindered non-nucleophilic phenol is 2,6-di-tertiary-butyl-4-methyl phenol.

* * * * *